United States Patent
Pinter et al.

(10) Patent No.: US 8,831,898 B2
(45) Date of Patent: Sep. 9, 2014

(54) IMPEDANCE MEASUREMENT CIRCUIT AND METHOD

(75) Inventors: Robert Pinter, Aachen (DE); Ralf Schmidt, Stuttgart (DE)

(73) Assignee: Koninklijke Philips N.V., Eindhoven (NL)

( * ) Notice: Subject to any disclaimer, the term of this patent is extended or adjusted under 35 U.S.C. 154(b) by 374 days.

(21) Appl. No.: 13/124,399

(22) PCT Filed: Oct. 8, 2009

(86) PCT No.: PCT/IB2009/054413
§ 371 (c)(1),
(2), (4) Date: Apr. 15, 2011

(87) PCT Pub. No.: WO2010/044026
PCT Pub. Date: Apr. 22, 2010

(65) Prior Publication Data
US 2011/0208458 A1    Aug. 25, 2011

(30) Foreign Application Priority Data

Oct. 16, 2008   (EP) .................................. 08166754

(51) Int. Cl.
  *G06F 19/00*   (2011.01)
  *A61B 5/053*   (2006.01)
(52) U.S. Cl.
  CPC ................................. *A61B 5/053* (2013.01)
  USPC .................................................. 702/65; 600/547
(58) Field of Classification Search
  CPC ............................................... A61B 5/053
  USPC .................................................................. 702/65
  See application file for complete search history.

(56) References Cited

U.S. PATENT DOCUMENTS

| | | | |
|---|---|---|---|
| 5,720,296 A | 2/1998 | Cha | |
| 5,735,284 A * | 4/1998 | Tsoglin et al. | ............... 600/513 |
| 2003/0149375 A1 | 8/2003 | Chen | |
| 2004/0054298 A1 | 3/2004 | Masuo et al. | |
| 2004/0181164 A1 | 9/2004 | Smith et al. | |
| 2008/0045854 A1 | 2/2008 | Weichao | |
| 2009/0051845 A1 | 2/2009 | Tsuchiyama | |

FOREIGN PATENT DOCUMENTS

| | | |
|---|---|---|
| EP | 1138258 | 10/2001 |
| JP | 2002153437 A | 5/2002 |
| WO | 200627360 | 3/2006 |

* cited by examiner

*Primary Examiner* — Bryan Bui

(57) ABSTRACT

An impedance measurement circuit comprises a current source arrangement, a voltage measurement arrangement and a processor. The circuit is operable in a two-point measurement mode and a four-point measurement mode and the processor is adapted to derive the impedance to be measured by combining the measurement voltages from the two-point and the four-point measurement modes. This combines the results of both two-point and four-point measurement techniques to provide improved accuracy. In particular, the two results enable the effect of the electrode resistance to be cancelled.

19 Claims, 3 Drawing Sheets

IMPEDANCE MEASUREMENT CIRCUIT AND METHOD

FIELD OF THE INVENTION

This invention relates to the measurement of impedance. Particularly but not exclusively, the invention relates to the measurement of impedance using surface contact electrodes.

BACKGROUND OF THE INVENTION

The measurement of impedance using surface contact electrodes presents a problem in that there are variable and unknown contact impedances, which reduce the accuracy of the measurement. Contact electrode impedance measurement is for example used in impedance measurement of skin tissue (so-called bio-impedance measurement), which can be used for monitoring various conditions relating to the physical or medical state of a user of the monitoring arrangement.

The simplest setup for measuring an impedance is the so-called two-point setup, which is shown in FIG. 1.

A measurement instrument 10 has a current source 12 which is used in order to feed a known current I into the unknown impedance $Z_X$. A voltage measurement using a voltage measurement device 14 determines the voltage drop, which is assumed to be proportional to the unknown impedance.

However, also the impedances $Z_W$ of the cables fully contribute to the voltage drop and to the measured voltage, thereby falsifying the measurement result Z:

$$Z=U/I=I*(Z_W+Z_X+Z_W)/I=Z_W+Z_X+Z_W>Z_X$$

As a result, the measurement result Z is higher than the true impedance $Z_X$. In order to avoid this disadvantage of the two-point impedance measurement setup, the four-point impedance measurement setup employs an additional pair of electrodes.

The four-point measurement technique is explained with reference to FIG. 2.

The current is fed through two feeding electrodes 1,4, (these can be considered as drive terminals) and the voltage drop is measured between two measurement electrodes 2,3 (these can be considered as measurement terminals). The voltage measurement is implemented with an instrument that has a very high input impedance (such as a high input impedance differential amplifier), so that almost no current flows through the measurement electrodes, i.e. their cables and contact resistance play almost no role in the measurement.

In this arrangement, one pair of electrodes is used to drive a current through the impedance to be measured, and another pair is used for the measurement, but without needing to draw significant current through the connections.

The measured voltage U is almost identical with the voltage drop $U_X$ at the unknown impedance $Z_X$. For many applications, the four-point impedance measurement setup thus provides sufficient accuracy. However, there are still errors in the measurement resulting from the current flow through the measurement electrodes 2,3.

SUMMARY OF THE INVENTION

According to the invention, there is provided an impedance measurement circuit comprising:
a current source arrangement;
a voltage measurement arrangement; and
a processor, wherein the circuit is operable in a two-point measurement mode and a four-point measurement mode, and
wherein the processor is adapted to derive the impedance to be measured by combining the measurement voltages from the two-point and the four-point measurement modes.

The invention thus combines the results of both two-point and four-point measurement techniques to provide improved accuracy. In particular, the two results enable the effect of the electrode resistance to be cancelled.

The two-point mode comprises a mode in which a first voltage across an impedance to be measured is obtained using a pair of measurement terminals which are used to route current to and from the impedance to be measured, and the four-point mode comprises a mode in which a second voltage across the impedance to be measured is obtained using the pair of measurement terminals, and with another pair of terminals used to route current to and from the impedance to be measured.

Thus, the two measurement techniques are individually standard, with the two electrodes of the two-point measurement mode being used as the measurement electrodes for the four-point mode.

A switching arrangement is preferably provided for switching a current output of a current source arrangement between a first pair of terminals and a second pair of terminals, the first pair of terminals comprising two-point impedance measurement terminals, and the first and second pair of measurement terminals together comprising four-point impedance measurement terminals.

The switching arrangement can have a first pair of inputs connected to opposite sides of the current source arrangement, and two pairs of outputs, the first pair of outputs comprising the two-point impedance measurement terminals and the second pair of outputs comprising the four-point measurement drive terminals.

Preferably, the processor is adapted to derive the impedance to be measured by calculating:

$$Z = \frac{Z_{fourpoint}}{\left[1 - \frac{Z_{twopoint}}{Ri}\right]}$$

wherein $Z_{fourpoint}$ is the four-point impedance derived from the four point measurement voltage, $Z_{twopoint}$ is the two-point impedance derived from the two point measurement voltage, and Ri is the internal impedance of the voltage measurement arrangement.

This relationship has been shown to cancel the effects of the electrode resistance.

The invention also provides a biosensor for measuring skin impedance, comprising:
a set of four contact electrodes for making contact with the skin; and an impedance measuring circuit according to the invention.

The invention also provides an impedance measurement method comprising:
obtaining a voltage measurement in a two-point measurement mode;
obtaining a voltage measurement in a four-point measurement mode;
deriving the impedance to be measured by combining the measurement voltages from the two-point and the four-point measurement modes.

This method can be used for bio-impedance sensing, by applying a set of four contact electrodes to make contact with the skin, and carrying out the method using two of the electrodes for the two-point measurement and using all four electrodes for the four-point measurement.

BRIEF DESCRIPTION OF THE DRAWINGS

An example of the invention will now be described in detail with reference to the accompanying drawings, in which.

The same reference numbers are used in different figures when they denote the same components. Where reference numbers are used in the claims, this is to improve the understanding of the claims and is not intended to be limiting.

DETAILED DESCRIPTION OF THE EMBODIMENTS

The invention provides an improvement to the two-point and four-point impedance measurement techniques, by combining the results of both measurement techniques to provide improved accuracy.

Figure 1:
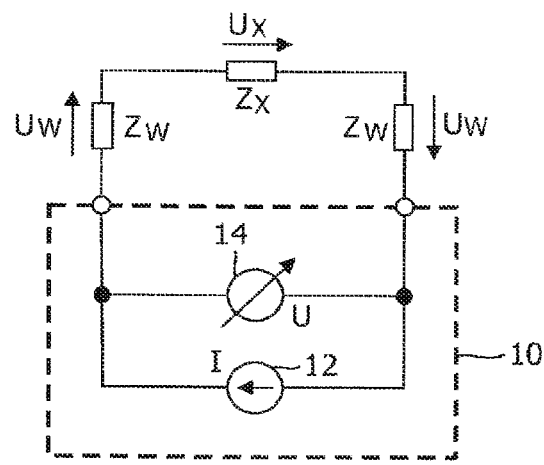
FIG. 1 is used to explain the known two-point measurement technique.
Figure 2:
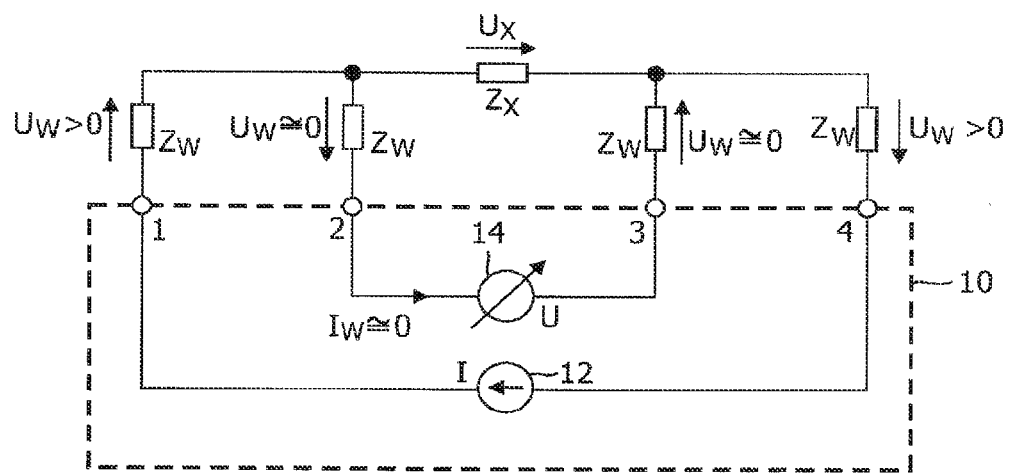
FIG. 2 is used to explain the known four-point measurement technique.
Figure 3:
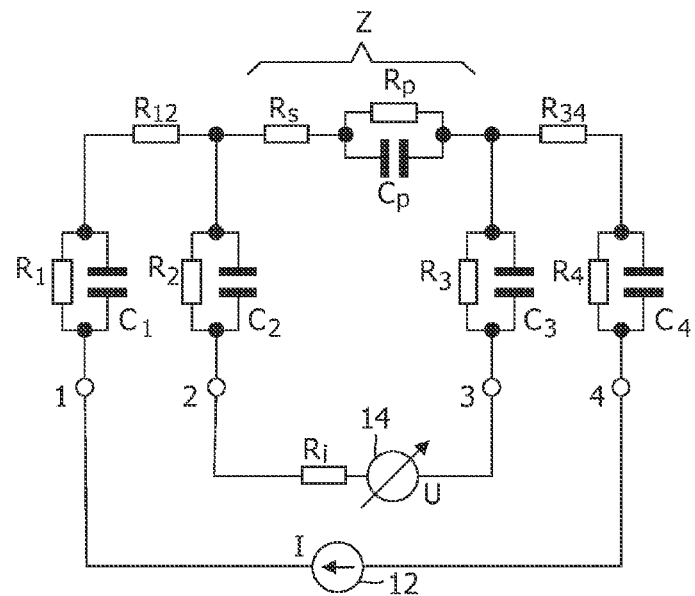
FIG. 3 is used to derive the errors resulting from the known four-point measurement technique.

The invention is based on the analysis of the error arising from the four-point impedance measurement process. FIG. 3 is used to explain the remaining error and shows the four-point setup ready to conduct an impedance measurement on an unknown object.

In this example, a known model of human tissue cells is used, in order to demonstrate the applicability of the invention for bio-impedance measurement applications, but in general, any unknown impedance can be considered.

The unknown impedance Z is modelled as a resistor $R_s$ in series with the combination of resistor $R_p$ and capacitor $C_p$ being in parallel with each other. At low frequencies, this model represents the cell impedance $R_s+R_p$, which at higher frequencies is reduced to only $R_s$. This happens because the cell membrane acts as a capacitor, represented here by the capacitor $C_p$.

Each electrode contact 1-4 is modelled by a resistor connected in parallel with a capacitor. The electrode can be considered to be a metal plate that is put on the skin. The electrode and the skin surface form the two plates of a capacitor, but of course they are not isolated from each other, and therefore represent a capacitor with losses, which is modelled by the resistor parallel to the capacitor.

As shown, there are resistors $R_{12}$ and $R_{34}$ modelling the tissue between the electrodes 1 and 2, 3 and 4, respectively. As will be shown below, these components don't play a role, which is the reason why they are modelled as simple resistors. A current source feeds a known current I into the terminals 1 and 4. A voltage measurement instrument with the high input impedance $R_i$ measures the voltage drop across the unknown impedance Z. In the following, the measured voltage U is calculated analytically, in order to understand the influence of the unwanted elements.

Figure 4:
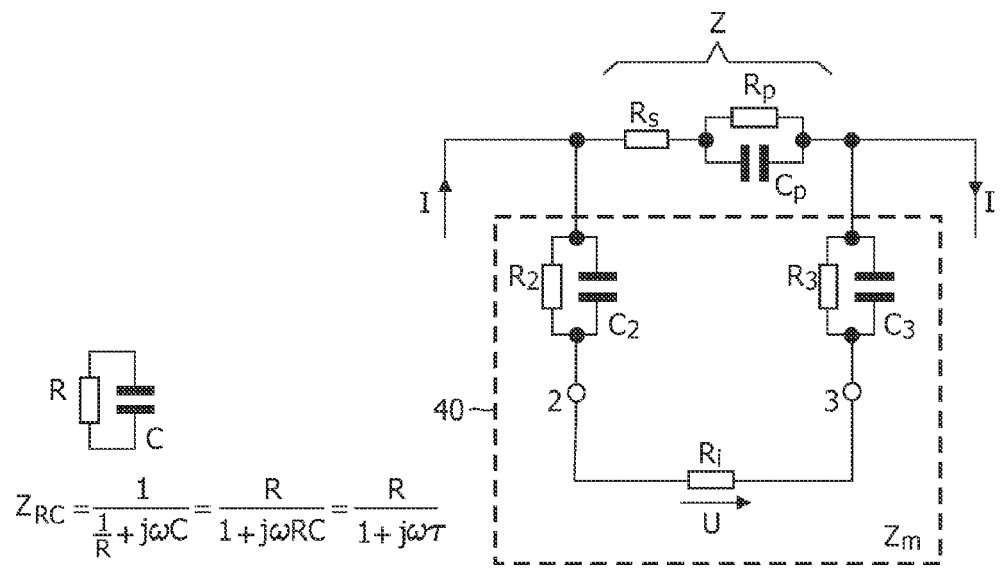
FIG. 4 is a simplified version of FIG. 3 showing the components relevant to the error analysis.

The known current flows unchanged through the electrodes at the terminals 1 and 4 and the resistors $R_{12}$ and $R_{34}$, so that the reduced schematic shown in FIG. 4 is applicable. Basically, there is now the unknown impedance Z connected in parallel with the network 40 (with combined impedance $Z_m$), which comprises the components inside the dashed line, and which can be described as:

$$Z_m = R_i + \frac{R_2}{1+j\omega\tau_2} + \frac{R_3}{1+j\omega\tau_3}; \tau_2 = R_2 \cdot C_2; \tau_3 = R_3 \cdot C_3 \quad \text{(Eq 1)}$$

For the total impedance of the network $Z_{total}$, i.e. $Z_m$ being connected in parallel with the unknown impedance Z, the following can be calculated.

$$Z_{total} = \frac{1}{\frac{1}{Z}+\frac{1}{Z_m}} = \frac{Z \cdot Z_m}{Z+Z_m} \quad \text{(Eq 2)}$$

The measured voltage U is a fraction of the voltage drop at this total impedance and can be calculated as:

$$U = \frac{R_i}{Z_m} \cdot Z_{total} \cdot I = \frac{R_i}{Z_m} \cdot \frac{Z \cdot Z_m}{Z+Z_m} \cdot I = \quad \text{(Eq 3)}$$
$$\frac{Z \cdot R_i}{Z+Z_m} \cdot I = \frac{R_i \cdot Z}{R_i + Z + \frac{R_2}{1+j\omega\tau_2} + \frac{R_3}{1+j\omega\tau_3}} \cdot I$$

The last two terms in the denominator, the terms with $R_2$ and $R_3$, falsify the result. The invention is based on the recognition that these errors can be determined. Once they are known, the unknown impedance Z can be calculated more precisely, because the resistor $R_i$ is a property of the measurement instrument and may therefore be assumed to be known.

The electrode contact quality can vary from measurement to measurement, so the terms with $R_2$ and $R_3$ in the equation above are not only unknown, but also variable. For many applications, it is possible to neglect those error terms. For applications requiring high measurement precision, however, the four-point setup as known in the state-of-the-art is not sufficient.

An example application, where high precision is required and where the electrode contact quality definitely varies from measurement to measurement, is a heart failure management system developed by the applicant. With the help of medication, the status of heart failure patients can be kept rather stable. However, over the course of time, the medication needs to be adjusted, and if this is not done in time, the patient will run into a so-called decompensation, meaning that the heart cannot sufficiently supply the body anymore, and liquid is accumulated in the limbs and in the lung. A costly hospitalization is the consequence in this case.

The concept for managing heart failure patients includes a bio-impedance measurement of the patient's chest every day, in order to detect liquid accumulating in the lung early enough to avoid a hospitalization by timely medication adjustment. A four-point measurement setup is used in order to conduct the daily measurements, and in order to achieve high repeatability of the setup, the electrodes are integrated into a harness that is put on like a vest.

Even though the position of the electrodes on the chest can be made substantially the same for every measurement with the help of the vest, the contact pressure will inevitably vary from measurement to measurement. If a state-of-the-art fourpoint measurement is employed under these changing conditions, measurement errors will result that can corrupt the whole heart failure management. This invention offers a reliable solution to this problem, but of course has much wider application to the accurate measurement of impedance more generally.

Figure 5:
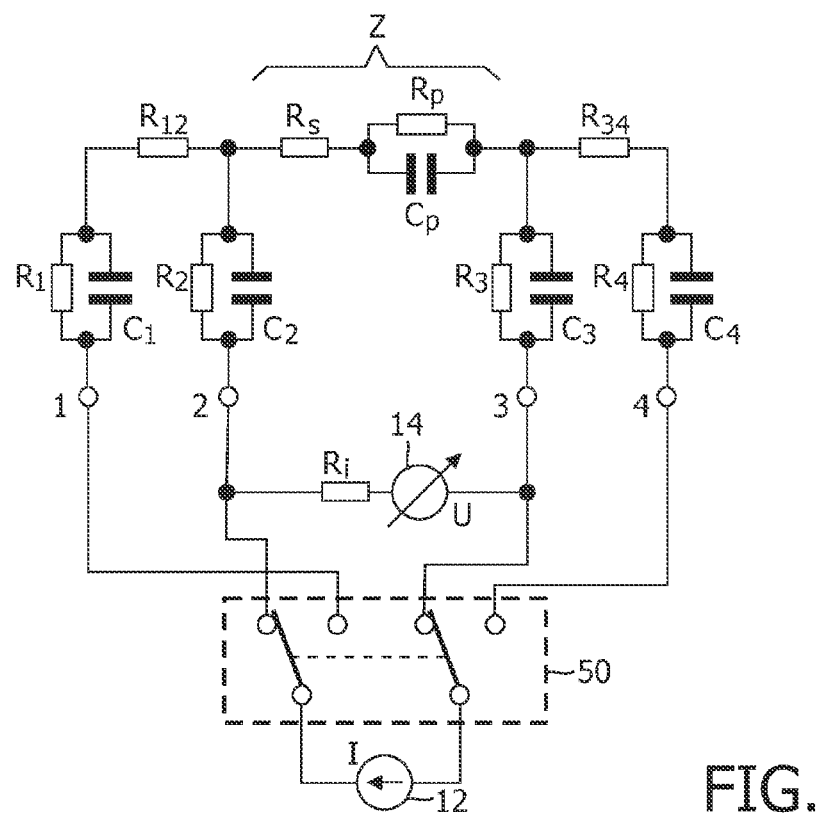
FIG. 5 is used to explain the measurement technique of the invention.

FIG. 5 shows the improved four-point impedance measurement setup, according to the invention. As can be seen, compared to the original setup, a switching unit 50 is provided that allows the current source 12 to be connected either to the terminals 1 and 4, so as to implement a conventional four-point measurement setup, or to the terminals 2 and 3, so as to conduct a two-point measurement using only the two measurement electrodes 2,3 of the four-point setup.

In order to precisely determine the unknown impedance Z, a procedure comprising two steps is provided. In the first step, a two-point measurement is conducted, with the current source being connected to terminals 2 and 3 by the switching unit 50. The measured voltage U is in this case:

$$U_{twopoint} = \frac{R_i \cdot \left[Z + \frac{R_2}{1+j\omega\tau_2} + \frac{R_3}{1+j\omega\tau_3}\right]}{R_i + \left[Z + \frac{R_2}{1+j\omega\tau_2} + \frac{R_3}{1+j\omega\tau_3}\right]} \cdot I_{twopoint} = \frac{R_i \cdot Z^+}{R_i + Z^+} \cdot I_{twopoint} \quad \text{(Eq. 4)}$$

The term $Z^+$ in the equation above describes the unknown error term in equation 3. Solving equation 4 for $Z^+$ yields:

$$Z_{twopoint} = \frac{U_{twopoint}}{I_{twopoint}} = \frac{R_i \cdot Z^+}{R_i + Z^+} \Rightarrow Z^+ = \frac{R_i \cdot Z_{twopoint}}{R_i - Z_{twopoint}} \quad \text{(Eq. 5)}$$

This expression is introduced into equation 3:

$$U_{fourpoint} = \frac{R_i \cdot Z}{R_i + Z + \frac{R_2}{1+j\omega\tau_2} + \frac{R_3}{1+j\omega\tau_3}} \cdot I_{fourpoint} = \frac{R_i \cdot Z}{R_i + Z^+} \cdot I_{fourpoint} \quad \text{(Eq. 6)}$$

By introducing equation 5, the following is obtained:

$$Z_{fourpoint} = \frac{U_{fourpoint}}{I_{fourpoint}} = \quad \text{(Eq. 7)}$$

$$\frac{R_i \cdot Z}{R_i + Z^+} = \frac{R_i \cdot Z}{R_i + \frac{R_i \cdot Z_{twopoint}}{R_i - Z_{twopoint}}} = \frac{Z}{1 + \frac{Z_{twopoint}}{R_i - Z_{twopoint}}}$$

$$Z_{fourpoint} = \frac{Z \cdot (R_i - Z_{twopoint})}{R_i - Z_{twopoint} + Z_{twopoint}} =$$

$$Z \cdot \left[1 - \frac{Z_{twopoint}}{R_i}\right] \Leftrightarrow Z = \frac{Z_{fourpoint}}{\left[1 - \frac{Z_{twopoint}}{R_i}\right]}$$

This shows that if the internal resistance of the voltage measurement circuit, $R_i$, is known, the result of the four-point measurement can be corrected using the result from the two-point measurement, so that the true value for the unknown impedance Z is obtained, by means of equation 7. $R_i$ can be a complex number, rather than a purely ohmic resistor.

In the second step of the procedure, the switching unit connects the current source to the terminals 1 and 4, thereby enabling a standard four-point measurement. The result of this four-point measurement can then be corrected, according to equation 7, using the result obtained before in the first step of the proposed procedure with the two-point measurement. Of course, the two and four point measurements can be performed in either order; the results are then combined to derive the correct impedance measurement.

The impedance Ri may be known from the equipment specifications. However, it is also possible to measure this value using the same circuit. When $R_i$ is unknown, a known impedance Z can be connected to the setup, and then a two-point measurement and a four-point measurement are conducted. Using equation 7, $R_i$ can then be calculated, based on the results from the two-point and the four-point measurement, according to the following:

$$Z = \frac{Z_{fourpoint}}{\left[1 - \frac{Z_{twopoint}}{R_i}\right]} \Leftrightarrow R_i = \frac{Z_{twopoint}}{\left[1 - \frac{Z_{fourpoint}}{Z}\right]} \quad \text{(Eq. 8)}$$

Since the impedance $R_i$ is a property of the measurement instrument, the calibration step described above, i.e. connecting a known impedance Z, conducting a two-point and a four-point measurement, and calculating $R_i$ thereof, needs to be done only once. Thus, the determination of Ri can be part of an initial calibration operation.

In subsequent measurements, only the two measurement steps described above need to be performed, i.e. a two-point measurement in one step, the result of which is used together with the previously determined $R_i$ according to equation 7 in order to correct the result obtained from the four-point measurement in the other step.

The two-point and four-point measurements should be conducted in rapid succession, so that the information about electrodes 2 and 3, which is contained in the measurement result of the two-point measurement, is valid for the time when the four point measurement is carried out.

This requirement is ensured by providing automated control of the two measurement steps, with the switching unit 50 controlled by a microcontroller that triggers the measurements.

Figure 6:
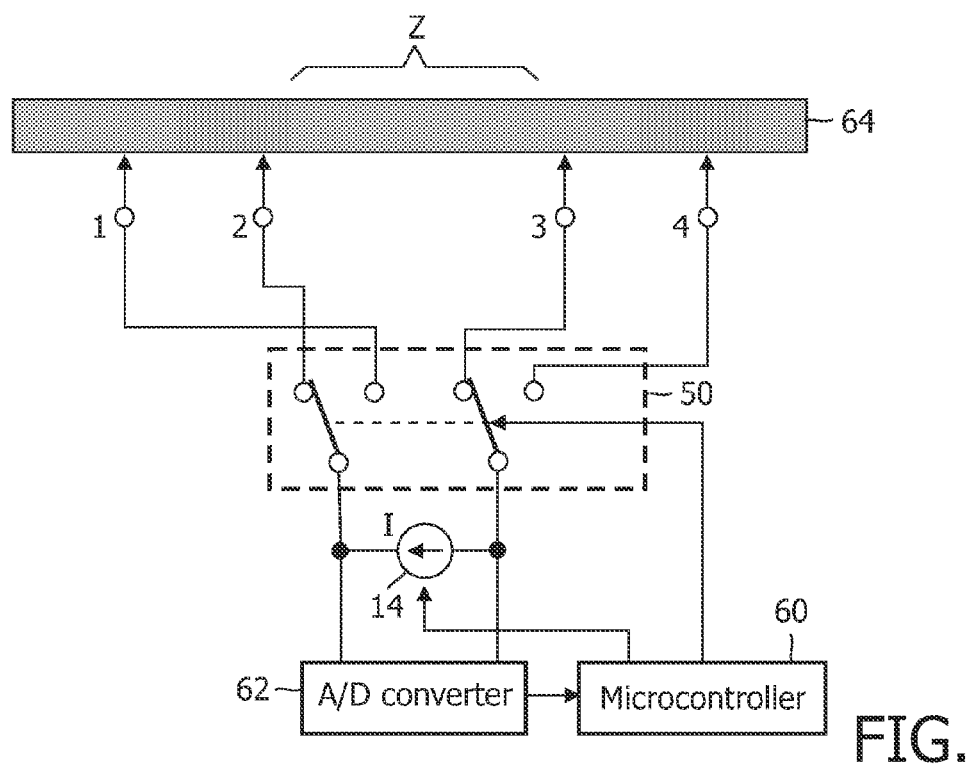
FIG. 6 shows an example of implementation of the measurement circuit of the invention.

FIG. 6 shows a block-diagram that gives an overview of the system.

The system comprises the switching arrangement 50 and current source 14. The switching arrangement connects the opposite sides of the current source either to the measurement electrodes 2,3 (as shown) or to the additional four-point electrodes 1,4. The switching arrangement is controlled by the microcontroller 60. The voltage measurement is carried out by the unit 62, which includes A/D conversion. The unit 62 is on the current source side of the switching arrangement 50, so that it is connected between the measurement electrodes 2,3 or the four-point electrodes 1,4 depending on the switch state.

The unit 62 provides the measurement results to the microcontroller 60, which implements the algorithm calculations explained above.

FIG. 6 shows the body 64 to which the electrodes 1-4 are applied, which in the example described above is the skin of the user.

The microcontroller not only controls the switching unit, but also controls the current source. The microcontroller can in this way vary parameters of the current source, for example the frequency of the current fed into the unknown impedance.

In this way, it is possible to conduct a whole series of measurements at different frequencies, whereby every single measurement comprises the abovementioned two steps, i.e. conducting a two-point measurement in order to obtain information about the electrode contact of the measurement electrodes at the terminals 2 and 3, and conducting a four-point measurement, the result of which is corrected by using the result from the two-point measurement obtained.

The advantage of the invention is that, except for the switching unit, no extra components have to be introduced into the system. The switching unit can for example be a relay, but also electronic switches (MOSFETs) can be used.

The invention improves on known four-point impedance measurements by improving the precision. One example of use of the invention is for measurements to be made for heart failure management. However, the invention more generally can be seen as an upgrade to state-of-the-art four-point impedance measurements. The approach compensates for the measurement error due to changing electrode contact quality, with minimal number of extra components required.

The switching arrangement is shown between the current source and the terminals. However, the invention could be implemented with two current sources (together forming a "current source arrangement"). Thus, the switching arrangement would then simply need to control one current source to be on when the other is off, or control only one of the two current sources to be connected in circuit. Thus, it will be seen that there are many ways to implement the switching arrangement, and the important requirement is that the circuit is adapted such that two and four point measurements can be made at different times.

The example described above relates to measurement of impedance using surface contact electrodes. However, the invention relates to impedance measurement more generally, and provides an improvement to known two- and four-point measurement techniques. Examples of potential application of the invention, in addition to the bio impedance sensing described above, fall into a number of categories, such as:

Health & Wellness Applications

Body fat/body composition measurements

De-hydration assessment (for example for sports training, diet assessment, health issues for the elderly)

Galvanic skin response/skin impedance measurement (for stress measurement or lie detection)

Emergency medical examinations (for example detection of internal bleeding in the thorax)

Monitoring and detection of bleeding in the body during the first few days after a surgery

INDUSTRIAL APPLICATIONS

Impedance measurement in order to detect corrosion of metals, e.g. in gas pipes.

There are many other examples, which will be apparent to those skilled in the art.

The current source used for the specific bio-sensing example given above is an ac current source. A typical range for the measurement frequency is then 5 kHz to 1 MHz. The maximum current is a function of the frequency, as described in the relevant standard about "Medical electrical equipment", IEC60601-1, and it also depends on the type of medical device.

For example, for devices classified as "BF", which have conductive contact with the patient such as electrodes, the following maximum values are indicated by the standard:

Below 1 kHz: maximum current value is 0.1 mA

Above 1 kHz: the maximum current is 0.1 mA multiplied by the frequency value in kHz (for example a frequency of 10 kHz gives rise to a maximum current of 1 mA)

Lower current values than the maximum can be used. However, a higher current gives the best signal-to-noise ratio.

The circuit elements have not been described in detail. The switching arrangement, current source and voltage measurement circuit, as well as the processor, are all standard components, and those skilled in the art will have no difficulty implementing the invention.

Various modifications will be apparent to those skilled in the art.

The invention claimed is:

1. An impedance measurement circuit comprising:
a current source arrangement;
a voltage measurement arrangement; and
a processor,
wherein the circuit is operable in a two-point measurement mode and a four-point measurement mode, and
wherein the processor is adapted to derive the impedance to be measured (Z) by combining the measurement voltages from the two-point and the four-point measurement modes by calculating a ratio of a four-point impedance derived from the four-point voltage measurement to a term that include a two-point impedance derived from the two-point voltage measurement.

2. The circuit as claimed in claim 1, wherein:
the two-point mode comprises a mode in which a first voltage across an impedance to be measured is obtained using a pair of measurement terminals) which are used to route current to and from the impedance to be measured; and
the four-point mode comprises a mode in which a second voltage across the impedance to be measured is obtained using the pair of measurement terminals, and with another pair of terminals used to route current to and from the impedance to be measured (Z).

3. The circuit as claimed in claim 1, comprising a switching arrangement for switching a current output of a current source arrangement between a first pair of terminals and a second pair of terminals, the first pair of terminals comprising two-point impedance measurement terminals, and the first and second pair of measurement terminals together comprising four-point impedance measurement terminals.

4. The circuit as claimed in claim 3, wherein the switching arrangement has a first pair of inputs connected to opposite sides of the current source arrangement, and two pairs of outputs, the first pair of outputs comprising the two-point impedance measurement terminals and the second pair of outputs comprising the four-point measurement drive terminals.

5. The circuit as claimed in claim 1, wherein the processor is adapted to derive the impedance to be measured by calculating:

$$Z = \frac{Z_{fourpoint}}{\left[1 - \frac{Z_{twopoint}}{Ri}\right]}$$

wherein $Z_{fourpoint}$ is the four-point impedance derived from the four point measurement voltage, $Z_{twopoint}$ is the two-point impedance derived from the two point measurement voltage, and Ri is the internal impedance of the voltage measurement arrangement.

6. The biosensor for measuring skin impedance, comprising:
 a set of four contact electrodes for making contact with the skin; and
 an impedance measuring circuit as claimed in claim 1.

7. An impedance measurement method comprising:
 obtaining a voltage measurement in a two-point measurement mode;
 obtaining a voltage measurement in a four-point measurement mode;
 deriving the impedance to be measured (Z) by combining the measurement voltages from the two-point and the four-point measurement modes by dividing a four-point impedance derived from the four-point measurement by a two-point impedance derived from the two-point measurement.

8. The method as claimed in claim 7, wherein:
 the two-point mode comprises obtaining a first voltage across an impedance to be measured using a pair of measurement terminals which are used to route current to and from the impedance to be measured; and
 the four-point mode comprises obtaining a second voltage across the impedance to be measured using the pair of measurement terminals, and using another pair of terminals in order to route current to and from the impedance to be measured (Z).

9. The method as claimed in claim 8, comprising switching a current source arrangement between a first pair of terminals and a second pair of terminals, the first pair of terminals comprising two-point impedance measurement terminals, and the first and second pair of measurement terminals together comprising four-point impedance measurement terminals.

10. The method as claimed in claim 7 wherein the processor derives the impedance to be measured by calculating:

$$Z = \frac{Zfourpoint}{\left[1 - \frac{Ztwopoint}{Ri}\right]}$$

wherein $Z_{fourpoint}$ is the four-point impedance derived from the four-point measurement voltage, $Z_{twopoint}$ is the two-point impedance derived from the two-point measurement voltage, and Ri is the internal impedance of the voltage measurement arrangement.

11. The method as claimed in claim 10, wherein the internal impedance Ri is obtained by performing the impedance measurement method using a known reference impedance to be measured.

12. The skin impedance measuring method, comprising:
 applying a set of four contact electrodes to make contact with the skin; and
 carrying out an impedance measuring method as claimed in claim 7 using two of the electrodes for the two-point measurement and using all four electrodes for the four-point measurement.

13. A non-transitory computer readable medium encoded with computer executable instructions, which, when executed by a computer processor, cause the computer processor to:
 obtain a two-point voltage measurement and a four-point voltage measurement;
 derive a two-point impedance from the two-point voltage measurement;
 derive a four-point impedance from the four-point voltage measurement; and
 derive an impedance to be measuring (Z) by calculating:

$$Z = \frac{Zfourpoint}{\left[1 - \frac{Ztwopoint}{Ri}\right]}$$

wherein $Z_{fourpoint}$ is the four-point impedance, $Z_{twopoint}$ is the two-point impedance, and Ri is the internal impedance of the voltage measurement arrangement.

14. The non-transitory computer readable medium as claimed in claim 13, wherein the internal impedance Ri a complex number.

15. The non-transitory computer readable medium as claimed in claim 13, wherein the four-point voltage is measured directly after the two-point voltage is measured.

16. The non-transitory computer readable medium as claimed in claim 13, wherein executing the computer executable instructions further causes the computer processor to:
 switch a current source arrangement between a first pair of terminals and a second pair of terminals, the first pair of terminals comprising two-point impedance measurement terminals, and the first and second pair of measurement terminals together comprising fourpoint impedance measurement terminals.

17. The non-transitory computer readable medium as claimed in claim 13, wherein executing the computer executable instructions further causes the computer processor to:
 calculate the internal impedance Ri by performing an impedance measurement with a known reference impedance.

18. The non-transitory computer readable medium as claimed in claim 17, the internal impedance Ri is calculated by:

$$Ri = \frac{Ztwopoint}{\left[1 - \frac{Zfourpoint}{Z_{ref}}\right]}$$

wherein $Z_{fourpoint}$ is the four-point impedance, $Z_{twopoint}$ is the two-point impedance, and Ri is the internal impedance, and $Z_{ref}$ is the known reference impedance.

19. The non-transitory computer readable medium as claimed in claim 17, wherein the internal impedance Ri calculation is part of an initial calibration operation.

* * * * *